(12) United States Patent
Jeong et al.

(10) Patent No.: US 12,290,769 B2
(45) Date of Patent: *May 6, 2025

(54) DIESTER-BASED MATERIAL PRODUCTION UNIT AND DIESTER-BASED MATERIAL PRODUCTION SYSTEM INCLUDING THE SAME

(71) Applicant: LG CHEM, LTD., Seoul (KR)

(72) Inventors: Jae Hun Jeong, Daejeon (KR); Sung Kyu Lee, Daejeon (KR); Yeon Uk Choo, Daejeon (KR); Hyoung Jun, Daejeon (KR); Hyun Kyu Kim, Daejeon (KR); Chan Hyu Jin, Daejeon (KR); Jin Sung Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 869 days.

This patent is subject to a terminal disclaimer.

(21) Appl. No.: 17/603,859

(22) PCT Filed: Jul. 2, 2020

(86) PCT No.: PCT/KR2020/008664
§ 371 (c)(1),
(2) Date: Oct. 14, 2021

(87) PCT Pub. No.: WO2021/002702
PCT Pub. Date: Jan. 7, 2021

(65) Prior Publication Data
US 2022/0220058 A1   Jul. 14, 2022

(30) Foreign Application Priority Data

Jul. 4, 2019   (KR) .......................... 10-2019-0080461

(51) Int. Cl.
*B01D 3/00*   (2006.01)
*B01D 3/06*   (2006.01)
*B01D 3/42*   (2006.01)
*B01D 53/00*   (2006.01)
*C07C 67/08*   (2006.01)
*C07C 67/52*   (2006.01)

(52) U.S. Cl.
CPC ............... *B01D 3/42* (2013.01); *B01D 3/009* (2013.01); *B01D 3/06* (2013.01); *B01D 53/00* (2013.01); *C07C 67/08* (2013.01); *C07C 67/52* (2013.01)

(58) Field of Classification Search
CPC . B01D 3/42; B01D 3/009; B01D 3/06; B01D 53/00; C07C 67/08; C07C 67/52;
(Continued)

(56) References Cited

U.S. PATENT DOCUMENTS 6,173,585 B1   1/2001   Billy et al.
12,122,747 B2 *  10/2024   Jeong ..................... C07C 67/52
(Continued)

FOREIGN PATENT DOCUMENTS

CN   107473967 A   12/2017
JP   2004-168978 A   6/2004
(Continued)

*Primary Examiner* — Huy Tram Nguyen
(74) *Attorney, Agent, or Firm* — Bryan Cave Leighton Paisner LLP (57) ABSTRACT

The present disclosure relates to a diester-based material production unit including a reaction device in which an esterification reaction of dicarboxylic acid and a primary alcohol is performed, a column in which the gas-liquid separation of the primary alcohol and the water introduced is performed, a heat exchanger installed on a gas phase line of the column to remove heat of the gas phase line, a flash drum in which separation of a liquid phase and a gas phase is performed in the mixture stream including the primary alcohol and the water, a condenser installed on the flash drum upper line, and a layer separator in which the layer separation of a mixture of a liquefied primary alcohol and water into an organic layer and an aqueous layer is performed, wherein one or more lines through which recirculated primary alcohol from the flash drum and the layer separator flows are connected to an upper portion of the (Continued)

column. According to the present invention, a coolant usage amount can be reduced and a rheological problem can be eliminated since a liquid phase and a gas phase coexist in a pipe.

10 Claims, 7 Drawing Sheets

(58) Field of Classification Search
CPC ......... C07C 67/48; C07C 69/82; Y02P 20/10; B01J 2219/0004; B01J 2219/00051; B01J 2219/00306
USPC .......................................................... 422/608
See application file for complete search history.

(56) References Cited

U.S. PATENT DOCUMENTS

| | | | |
|---|---|---|---|
| 2009/0012327 A1 | 1/2009 | Tanaka et al. | |
| 2009/0264671 A1* | 10/2009 | Noh ........................ | C11C 1/005 560/129 |
| 2011/0269997 A1 | 11/2011 | Cox et al. | |
| 2013/0197266 A1 | 8/2013 | Gadewar et al. | |
| 2015/0330706 A1 | 11/2015 | Vermeiren et al. | |
| 2017/0297998 A1 | 10/2017 | Schraut et al. | |
| 2019/0024971 A1 | 1/2019 | Vermeiren et al. | |
| 2019/0263745 A1 | 8/2019 | Lee et al. | |
| 2021/0040026 A1 | 2/2021 | Lee et al. | |

FOREIGN PATENT DOCUMENTS

| | | |
|---|---|---|
| JP | 4158396 B2 | 10/2008 |
| JP | 2012-211177 A | 11/2012 |
| KR | 10-1995-0005797 A | 3/1995 |
| KR | 10-0122429 B1 | 11/1997 |
| KR | 10-2000-0006459 A | 1/2000 |
| KR | 10-2011-0047189 A | 5/2011 |
| KR | 10-2015-0095677 A | 8/2015 |
| KR | 10-1663586 B1 | 10/2016 |
| KR | 10-2018-0074984 A | 7/2018 |
| KR | 10-2019-0027622 A | 3/2019 |
| KR | 10-2019-0027623 A | 3/2019 |

* cited by examiner

DIESTER-BASED MATERIAL PRODUCTION UNIT AND DIESTER-BASED MATERIAL PRODUCTION SYSTEM INCLUDING THE SAME

CROSS-REFERENCE TO RELATED APPLICATIONS

This application is a National Phase entry pursuant to 35 U.S.C. § 371 of International Application No. PCT/KR2020/008664, filed on Jul. 2, 2020, and claims the benefit of and priority to Korean Patent Application No. 10-2019-0080461, filed on Jul. 4, 2019, in the Korean Intellectual Property Office, all of which are hereby incorporated by reference in their entirety for all purposes as if fully set forth herein.

TECHNICAL FIELD

Technical Field

The present invention relates to a diester-based material production unit with an improved reflux system and a diester-based material production system including the same.

Background Art

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer can be leaked little by little out of the product and act as a suspected endocrine disruptor (environmental hormone) and a carcinogen to the level of a heavy metal (N R Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of a phthalate-based plasticizer, di(2-ethylhexyl) phthalate in particular, many researchers have been conducting research in order to develop a new non-phthalate-based alternative plasticizer without phthalic anhydride used in the manufacturing of di(2-ethylhexyl) phthalate, and to develop a phthalate-based plasticizer which can replace di(2-ethylhexyl) phthalate and be used for industrial purposes since the leakage of the plasticizer is suppressed even though it is based on phthalate, as well as to develop a leakage suppression technology which suppresses the leakage of phthalate-based plasticizers, thereby significantly reducing risks to human bodies and which meets environmental standards.

As such, as diester-based plasticizers, the development of materials which are free from environmental problems and which can replace a di(2-ethylhexyl) phthalate having existing environmental problems is actively underway. In addition, research on developing a diester-based plasticizer with excellent physical properties as well as research on equipment for manufacturing the plasticizer have been actively conducted, and there has been a demand for more efficient, more economical and simpler process designs in terms of process design.

Meanwhile, a batch process is being applied in most industrial sites as a process of producing the above diester-based plasticizer. As the batch process, an invention related to a gas-liquid separation system for the reflux of non-reactants and efficient removal of sub-reactants in a reactor (Korean Patent Laid-Open Publication No. 10-2019-0027622) and an invention related to a system integrating facilities of a primary direct esterification reaction and a second trans-esterification reaction in order to simplify facilities of a batch process (Korean Patent Laid-Open Publication No. 10-2019-0027623) have been introduced. However, as a batch process, such inventions have limitations in that there is a limit to the improvement in the amount of reflux or the volume of steam, the productivity is very low, and there is a limit to the technology which can be applied for improvement.

In addition, as a continuous process, an invention related to a process configuring a reaction part by connecting two or more reactors in series (Korean Patent Publication No. 10-1663586) has also been introduced. However, there is a limit to improving the overall processability only by controlling the reaction temperature of continuously connected reactors.

PRIOR ART DOCUMENT

Patent Document (Patent Document 1) Korean Patent Laid-Open Publication No. 10-2019-0027622
(Patent Document 2) Korean Patent Laid-Open Publication No. 10-2019-0027623
(Patent Document 3) Korean Patent Laid-Open Publication No. 10-1663586

DISCLOSURE OF THE INVENTION

Technical Problem

An aspect of the present invention provides a diester-based material production unit and a diester-based material production system including the same, in which a reflux system is applied to the diester-based material production unit applied to a process of continuously producing a diester-based material, the reflux system including a flash drum and improved by selecting an appropriate position of a stream to be refluxed, so that a rheological problem which can occur due to the coexistence of a liquid and a gas in a pipe or a condenser is solved, a coolant usage amount can be greatly reduced even when the amount of reflux is large, and an alcohol to be refluxed can have a temperature maintained to be higher than usual and supplied.

Technical Solution

According to an aspect of the present invention, there is provided a diester-based material production unit including a reaction device including a reaction vessel in which an esterification reaction of dicarboxylic acid and a primary alcohol is performed and a gas phase discharge line installed at an upper end of the reaction vessel such that vaporized primary alcohol and water are discharged to a column therethrough, the column including a column main body in which the gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a side portion of a flash drum such that a mixture stream of a gas-phase primary alcohol and water flows out, a heat exchanger installed on the gas phase line of the column to remove heat of the gas phase line, the flash drum having a flash drum main body in which separation of a liquid phase and a gas phase is performed in the mixture stream including the primary alcohol and the water, a flash drum lower line from which the liquid phase including a liquefied primary alcohol is discharged, a flash drum upper line installed to discharge the mixture stream of the gas-phase primary alcohol and the water to a layer separator, a condenser installed on the flash drum upper line to liquefy the mixture of the gas-phase primary alcohol and the water in the line, and the layer separator including a separation tank in which the layer separation of a mixture of the liquefied primary alcohol and the water into an organic layer and an aqueous layer is performed, an organic layer line through which the separated organic layer is discharged, an aqueous layer line through which the separated aqueous layer is discharged.

The flash drum lower line of the flash drum of the diester-based material production unit is connected to one or more positions selected from the group consisting of a column main body side upper portion, a column main body side lower portion, and the reaction vessel.

The organic layer line of the layer separator of the diester-based material production unit is connected to one or more positions selected from the group consisting of a flash drum main body side portion, the column main body side upper portion, the column main body side lower portion and the reaction vessel.

One or more of the flash drum lower line and the organic layer line of the diester-based material production unit are connected to the column main body side upper portion.

Advantageous Effects

The present invention employs an improved reflux system, and thus, can solve a rheological problem which can occur due to the coexistence of a liquid and a gas in a pipe and a condenser, greatly reduce coolant usage amount even when the amount of reflux is large, and reduce the volume of steam in a reactor by maintaining the temperature of an alcohol to be refluxed to be higher than usual.

MODE FOR CARRYING OUT THE INVENTION

Hereinafter, the present invention will be described in more detail to facilitate understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor can properly define the meaning of the words or terms to best explain the invention.

A diester-based material production unit according to an embodiment of the present invention includes a reaction device including a reaction vessel in which an esterification reaction of dicarboxylic acid and a primary alcohol is performed and a gas phase discharge line installed at an upper end of the reaction vessel such that vaporized primary alcohol and water are discharged to a column therethrough, a column including a column main body in which the gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a side portion of a flash drum such that a mixture stream of a gas-phase primary alcohol and water flows out, a heat exchanger installed on the gas phase line of the column to remove heat of the gas phase line, a flash drum having a flash drum main body in which separation of a liquid phase and a gas phase is performed in the mixture stream including the primary alcohol and the water, a flash drum lower line from which the liquid phase including a liquefied primary alcohol is discharged, a flash drum upper line installed to discharge the mixture stream of the gas-phase primary alcohol and the water to the layer separator, a condenser installed on the flash drum upper line to liquefy the mixture of the gas-phase primary alcohol and the water in the line, and a layer separator including a separation tank in which the layer separation of a mixture of the liquefied primary alcohol and the water into an organic layer and an aqueous layer is performed, an organic layer line through which the separated organic layer is discharged, an aqueous layer line through which the separated aqueous layer is discharged.

In addition, the flash drum lower line of the flash drum is connected to one or more positions selected from the group consisting of a column main body side upper portion, a column main body side lower portion, and the reaction vessel, the organic layer line of the layer separator of the diester-based material production unit is connected to one or more positions selected from the group consisting of a flash drum main body side portion, the column main body side upper portion, and the column main body side lower portion, and one or more of the flash drum lower line and the organic layer line are connected to the column main body side upper portion.

In applying a system which sends gas-phase materials such as an alcohol to be refluxed to an upper portion of a reactor back to the reactor in a typical diester-based material production process, a system which recovers heat by installing a heat exchanger at an upper portion of a column and then sends the recovered heat back to a reactor through further performing liquefaction and layer separation after the liquefaction is generally applied.

In this case, in the process of recovering heat from a gas-phase material at the upper portion of the column using the heat exchanger, a portion of a gas phase is liquefied in a line and another portion thereof remains in a gas phase, and thus, a liquid phase and a gas phase coexist in a pipe thereby causing a problem with the flow of a fluid, a problem in which the efficiency of the condenser is greatly deteriorated due to the presence of the liquid phase relatively slow in heat transfer in a line occurs.

Accordingly, in the production unit according to an embodiment of the present invention, a liquid phase generated in a line after heat exchange is not immediately introduced into a layer separator but is subjected again to gas-liquid separation through a flash drum, so that a rheological problem of fluid flow in the line can be solved without deteriorating the efficiency of the condenser. In addition, before the layer separation which is performed after liquefaction and cooling through the condenser is performed, some non-reactants can be refluxed to a column and/or a reaction device from the flash drum, and thus, a refluxed non-reactant (e.g., alcohol) can be re-injected into the reactor while the temperature thereof is maintained to be high, so that the reduction in the volume of steam used in the reactor can also be achieved when the amount of reflux is the same.

Hereinafter, the diester-based material production unit according to an embodiment of the present invention will be described with reference to the accompanying drawings.

Figure 1:
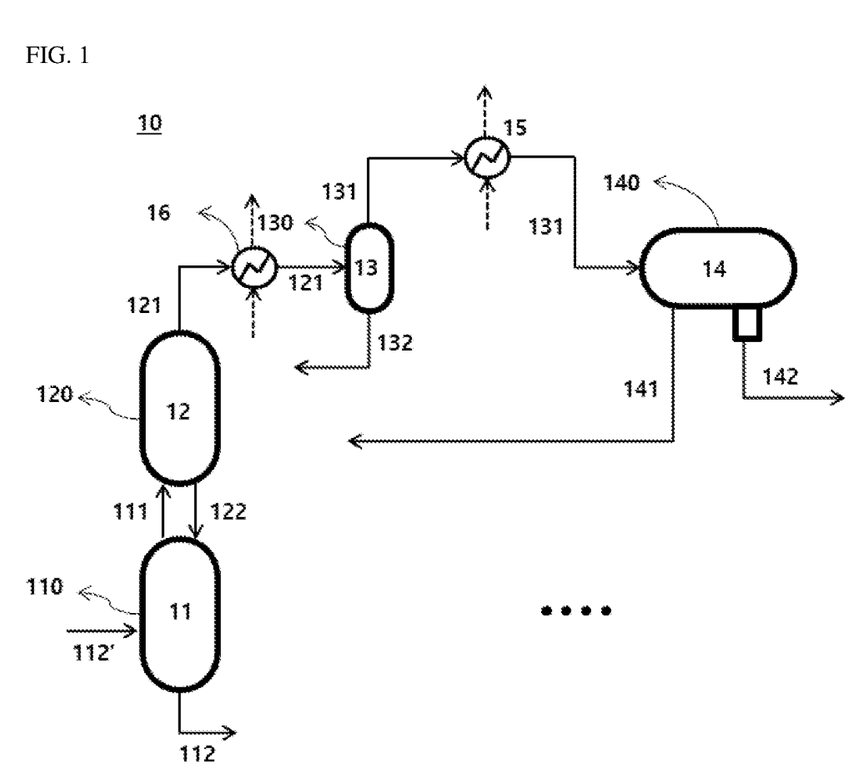
FIG. 1 is a process diagram showing a production unit of a diester-based material according to an embodiment of the present invention.

FIG. 1 is a process diagram showing a production unit 10 of a diester-based material according to an embodiment of the present invention. A facility in which a diester-based material is produced includes a reaction device 11 in which an esterification reaction of dicarboxylic acid and a primary alcohol is performed, a column 12 in which gas-liquid separation is performed by pulling up an alcohol, which is a non-reactant vaporized during a reaction, and water, which is a side-reactant, a heat exchanger 16 for recovering heat of a gas phase line 121 discharged to an upper portion of the column, a flash drum 13 for performing gas-liquid separation of a liquefied primary alcohol and a mixture of a gas-phase primary alcohol and water on a line to return a liquid phase present in the line to the reaction device before layer separation, a condenser 15 for liquefying all of the mixture of the gas-phase primary alcohol and the water before introducing the same into a layer separator, and a layer separator 14 for separating the mixture of the liquefied primary alcohol and the water through layer separation.

Specifically, the production unit 10 includes the reaction device 11, and the reaction device 11 includes a reaction vessel 110 in which an esterification reaction of dicarboxylic acid and a primary alcohol is performed, and a gas phase discharge line 111 installed at an upper end of the reaction vessel 110 through which vaporized primary alcohol and water are discharged to a column.

The reaction device 11 can also have a raw material injection line 112' through which dicarboxylic acid and a primary alcohol, which are raw materials, are injected, and a product line 112 for sending a product to a reaction device of the next production unit if a plurality of production units are provided, or to a purification unit when there is a single production unit or when it is the last production unit of a plurality of production units.

However, the raw material injection line 112' can have a pre-mixer (not shown) further installed at a front end of an initial production unit to inject raw materials into the pre-mixer, thereby supplying the raw materials to a reaction device, or can supply raw materials by performing line mixing with one raw material input line. Alternatively, raw materials can be supplied through different injection lines for each raw material. The injection method of raw materials is not particularly limited as long as it is a method capable of supplying raw materials into a reaction device.

In addition, the production unit 10 includes the column 12, and the column 12 connected to the reaction device 11 through the gas phase discharge line 111 includes a column main body 120 in which the gas-liquid separation of the primary alcohol and the water introduced from the gas phase discharge line 111 is performed, a liquid phase line 122 installed at a lower portion of the column main body 120 such that a liquefied alcohol-rich stream flows into the reaction device, and a gas phase line 121 installed at an upper portion of the column main body 120 and connected to a side portion of the flash drum 13 such that a mixture stream of the gas-phase primary alcohol and the water flows out.

In the reaction device 11, an esterification reaction is performed in the reaction vessel 110, and the reaction can be performed at a temperature of about 150° C. to 230° C. by having dicarboxylic acid and a primary alcohol as raw materials. The dicarboxylic acid, which is a raw material, can include one or more selected from the group consisting of terephthalic acid, phthalic acid, isophthalic acid, and cyclohexane dicarboxylic acid, and the primary alcohol which is another raw material can have 3 to 10 carbon atoms.

When the raw materials are used to perform an esterification reaction, the reaction temperature of the esterification reaction can be higher than the boiling point of the primary alcohol having 3 to 10 carbon atoms applied as a raw material, so that the vaporization of the primary alcohol inevitably occurs during the reaction. In addition, due to the evaporation of the primary alcohol, a problem in which reactants are continuously decreased in a reaction vessel occurs. Therefore, the reaction is performed by injecting an excess amount of the primary alcohol above an equivalent ratio in theory.

Accordingly, the molar ratio of the dicarboxylic acid and the primary alcohol in a reaction part (particularly a first reaction part in a production system to be described later) can be 1:2 to 1:5, and can be to prevent energy loss due to unnecessary reflux caused by the injection of an excessive amount of alcohol and can be determined in consideration of the excess amount of alcohol required in terms of achieving the conversion rate of the reaction and controlling the minimum residence time. The molar ratio can preferably be 1:2 to 1:4, and in order to optimally reflect the above, a molar ratio of 1:2.5 to 1:4 can be applied.

In addition, the esterification reaction generates water as a side-reactant, but the generation of water, on the contrary, can accelerate a reverse reaction and become the cause to interfere with the achievement of a target conversion rate, and thus, it can also be important to remove the water from a reaction vessel.

That is, gas-phase water generated during the reaction should be removed in the reaction device 11, and inevitably, the operation to re-liquefy the vaporized primary alcohol and return the re-liquefied primary alcohol to the reactor is essential. Accordingly, the column 12 is installed at an upper portion of the reaction device 11.

In the column 12, the gas-liquid separation of the vaporized primary alcohol and the water is performed. The mixture of the gas-phase primary alcohol and the water is introduced to a lower portion of the column main body 120 of the column 12 from the gas phase discharge line 111 at the upper portion of the reaction vessel 110, and the introduced gas-phase mixture ascends in the column main body 120 of the column 12 and comes in contact with a liquid-phase primary alcohol descending from a side upper portion of the column 12, so that the primary alcohol and the water are separated into the lower portion of the column main body 120 and the upper portion of the column main body 120, respectively. Here, the liquid-phase primary alcohol descending from an upper portion of the column 12 can be supplied from a flash drum 13 at a rear end or from a layer separator 14.

The primary alcohol and the water vaporized in the reaction device 11 are primarily separated through the gas-liquid separation in the column 12, and the liquefied primary alcohol is supplied back to the reactor 110 through the liquid phase line 122, and thus, can participate in the reaction. In addition, a mixture gas of water still in gas phase and unseparated primary alcohol is discharged through the gas phase line 121 at the upper portion of the column. At this time, the temperature of an internal gas phase mixture stream discharged through the gas phase line 121 can be about 130° C. to 180° C. Although a portion of the primary alcohol is liquefied and returned to the reactor, the primary alcohol can still be excessive, and thus, the weight ratio of the primary alcohol to the water can be about 1 or more.

The production unit 10 includes a heat exchanger 16 for recovering the heat of the gas phase line 121 of the column and transferring the same to another place which needs heat supply in the process, and the heat exchanger 16 is installed on the gas phase line 121 of the column 12. The mixture stream of the gas-phase water and primary alcohol discharged through the gas phase line 121 from the column should be eventually liquefied such that the primary alcohol is refluxed and the water is removed, which is a stream from which heat should be removed. However, when heat is removed by only a condenser, energy loss is large. Therefore, it is preferable to perform an operation of transferring the heat of the mixture stream in the gas phase line to another place in the process through the heat exchanger 16 and removing the heat.

Meanwhile, when heat is removed from a stream in the gas phase line 121 as described above, liquefaction can occur, in which case a phenomenon in which a liquid and a gas coexist within the line can occur. However, when a gas and a liquid coexist in a pipe, a rheological problem can occur therein, and there is also a problem in which cooling efficiency is considerably lowered due to the presence of a liquid phase in removing residual heat through the condenser afterwards.

Therefore, in the present invention, the flash drum 13 is introduced to solve the above problem. Since the primary alcohol liquefied by the heat exchanger 16 can be immediately recirculated through the flash drum 13 before passing through the condenser 15, the rheological problem in the pipe or the problem of the efficiency deterioration of the condenser cannot occur.

The flash drum 13 connected to the column 12 through the gas phase line 121 has a flash drum main body 130 in which the mixture stream including partially liquefied primary alcohol and water by the heat exchanger 16 is subjected to gas-liquid separation, a flash drum lower line 132 through which a liquid phase including the liquefied primary alcohol is discharged, and a flash drum upper line 131 installed to discharge a mixture stream of the gas-phase primary alcohol and the water to the layer separator 14.

The flash drum 13 can perform the gas-liquid separation inside the flash drum main body 130, and can return a large amount of primary alcohol to the reactor through simple equipment and treatment. At this time, the liquefied primary alcohol can be recovered to the reaction system through the reaction device 11 or the column 12 through the flash drum lower line 132. Since the temperature of the primary alcohol recovered from the flash drum 13 is higher than that by condensation and cooling, even if the primary alcohol is recovered to the reactor, it is possible to minimize the temperature change in the reaction system. Also, since a portion of the primary alcohol is primarily separated, the amount of cooling water used in the condenser can be greatly reduced, and thus, the energy saving effect obtained through the introduction of the flash drum 13 can be significant.

In addition, the production unit 10 includes the layer separator 14. The layer separator 14 connected to the flash drum 13 through the flash drum upper line 131 includes a separation tank 140 in which a gas phase discharged from the upper portion of the flash drum is liquefied to perform layer separation into an organic layer and an aqueous layer, an organic layer line 141 from which the separated organic layer is discharged, and an aqueous layer line 142 from which the separated aqueous layer is discharged.

Furthermore, the production unit 10 includes a condenser 15 for performing cooling and condensing such that a stream flowing through the flash drum upper line 131 of the flash drum 13 is liquefied before being introduced into the layer separator 14, and the condenser 15 is installed on the flash drum upper line 131. The liquefied liquid-phase primary alcohol and water are separated into an organic layer of the primary alcohol and an aqueous layer of the water in the separation tank 140 of the layer separator 14.

The primary alcohol in the organic layer can be recirculated to the flash drum 13, column 12, or the reaction device 11 through the organic layer line 141, and the temperature of a primary alcohol stream in the organic layer line can be about 40° C. to about 95° C. Typically, reflux is achieved only through the layer separator 14 without the recirculation of a primary alcohol by the flash drum 13, so that when the recirculated primary alcohol is introduced into a reaction system, the reaction temperature is lowered, and thus, additional steam supply to the reactor is required. However, in the present invention, since the temperature of the primary alcohol recirculated from the flash drum 13 is relatively high, an effect of energy saving can be additionally expected.

In addition, the water in the aqueous layer is discharged from the separation tank 14 through the aqueous layer line 142. At this time, the discharged water can be used to produce steam through an additional separation facility as generated water in the process and there is no particular limitation to the utilization of the water after being removed from the reaction device.

The production unit 10 according to one embodiment of the present invention includes a flash drum lower line 132 of the flash drum 13 and the organic layer line 141 of the layer separator 14 as lines for subjecting a primary alcohol to reflux, that is, recirculation. In returning the primary alcohol to the reaction device 11, the recirculation lines can be connected at various positions. The flash drum lower line 132 is connected to one or more positions selected from the group consisting of a side upper portion of the column main body 120, a side lower portion of the column main body 120, and the reaction vessel 110, and the organic layer line 141 is connected to one or more positions selected from the group consisting of a side portion of the flash drum main body 130, the side upper portion of the column body main 120, the side lower portion of the column main body 120, and a reaction vessel 110.

At this time, any one of the flash drum lower line 132 and the organic layer line 141 is necessarily to be connected to the side upper portion of the column main body 120 of the column 12. This is because gas-liquid separation can be performed only when a gas phase ascends in a lower portion and a liquid phase descends in an upper portion of the column main body 120 of the column 12.

FIG. 2 to FIG. 7 show an example of connecting a line such that the flash drum lower line 132 and the organic layer line 141 are finally introduced into the reaction device 11.

Figure 2:
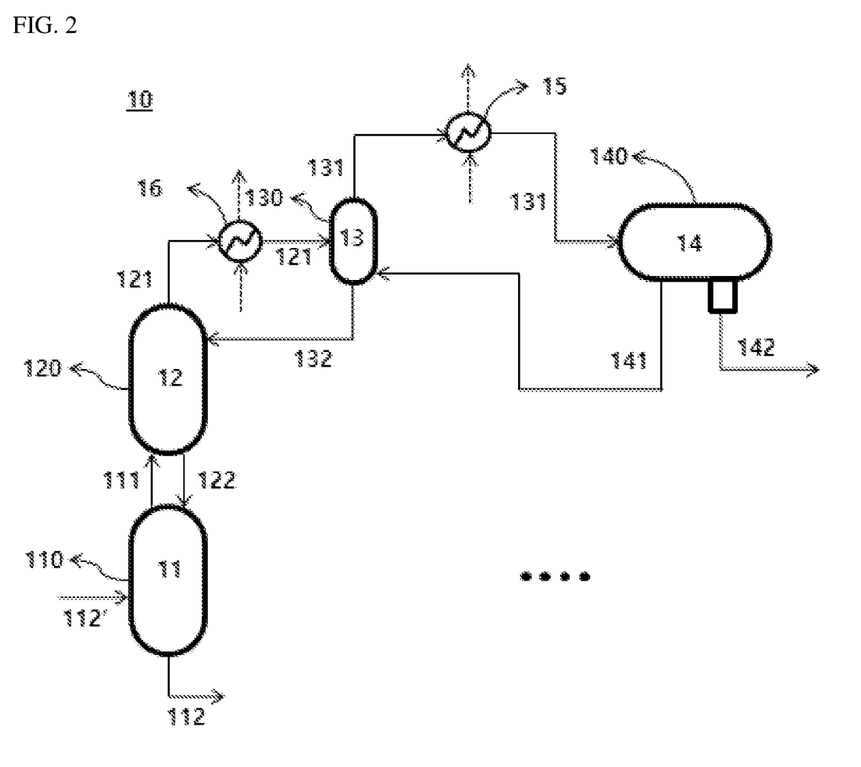
FIG. 2 is a process diagram showing an example of selecting positions of a flash drum lower line and an organic layer line of a diester-based material production unit according to an embodiment of the present invention.
Figure 3:
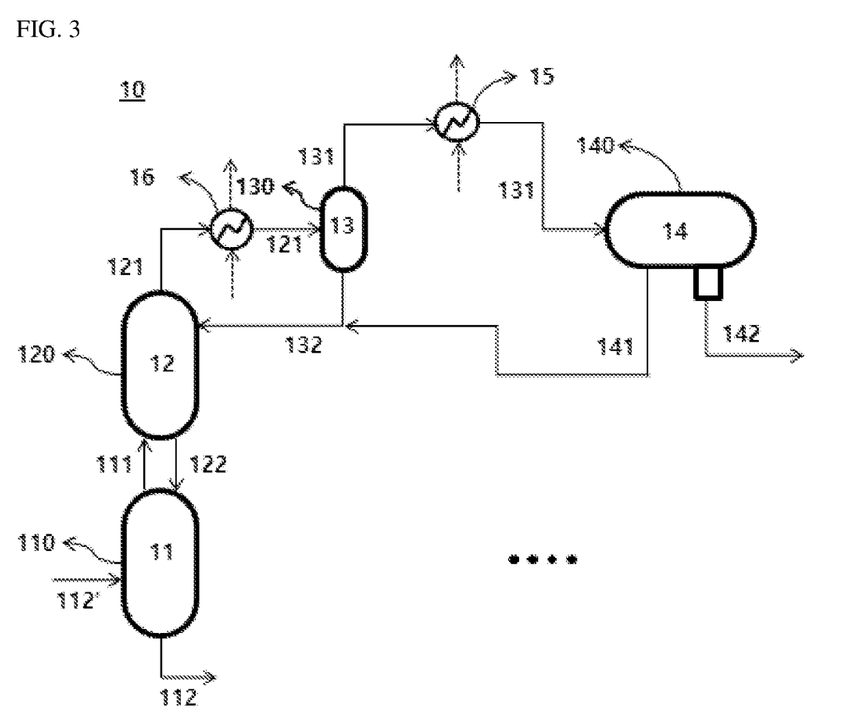
FIG. 3 is a process diagram showing an example of selecting positions of a flash drum lower line and an organic layer line of a diester-based material production unit according to an embodiment of the present invention.
Figure 4:
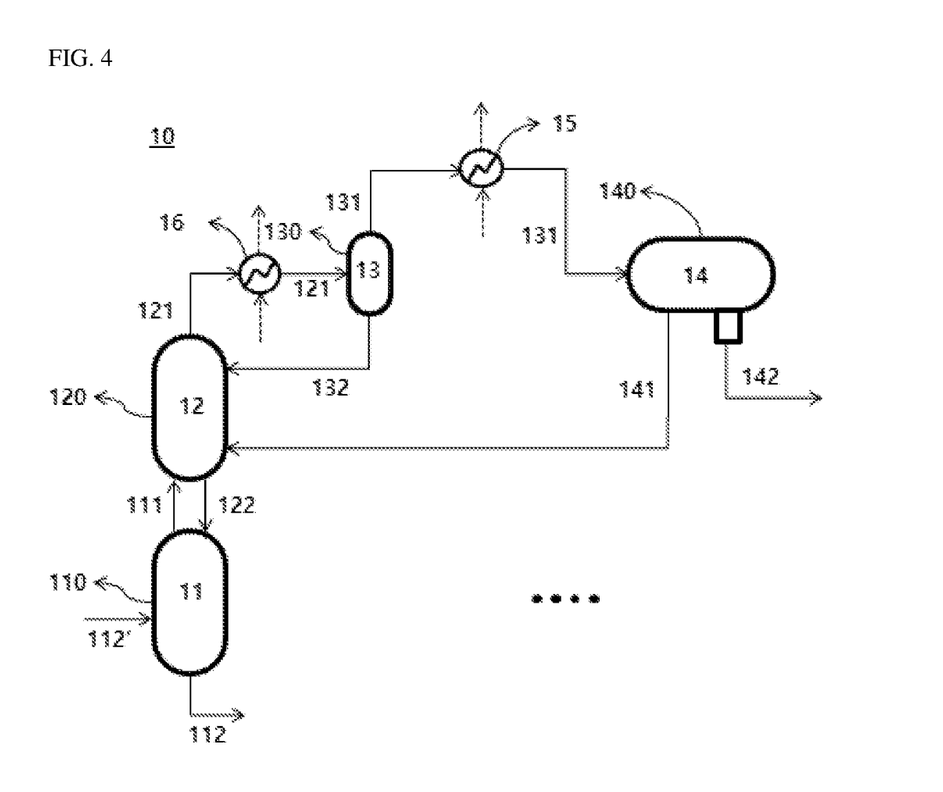
FIG. 4 is a process diagram showing an example of selecting positions of a flash drum lower line and an organic layer line of a diester-based material production unit according to an embodiment of the present invention.

FIG. 2 illustrates that the flash drum lower line 132 is connected to the side upper portion of the column main body 120 of the column 12 and the organic layer line 141 is connected to the side portion of the flash drum main body 130 of the flash drum 13. FIG. 3 illustrates that while the connection of the flash drum lower line 132 is the same, the organic layer line 141 is configured to be connected to the flash drum lower line 132 rather than the side portion of the flash drum main body such that a primary alcohol is recirculated though a line connection. FIG. 4 also illustrates that the connection of the flash drum lower line 132 is the same and the organic layer line 141 is connected to the side lower portion of the column main body 120 of the column 12.

Figure 5:
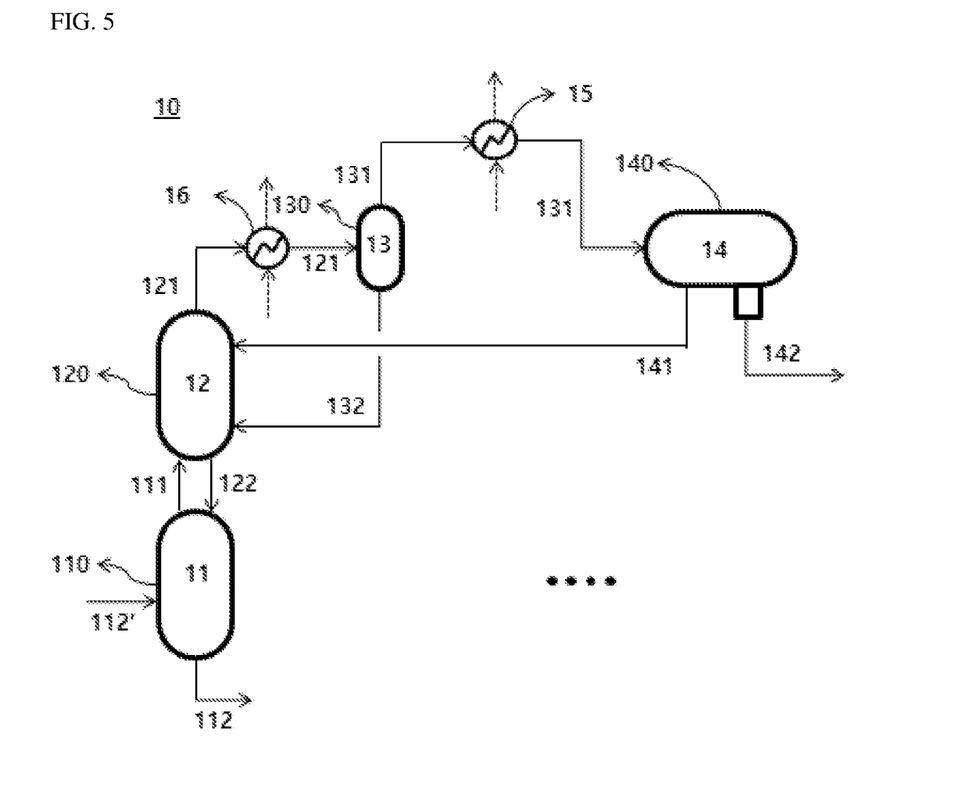
FIG. 5 is a process diagram showing an example of selecting positions of a flash drum lower line and an organic layer line of a diester-based material production unit according to an embodiment of the present invention.
Figure 6:
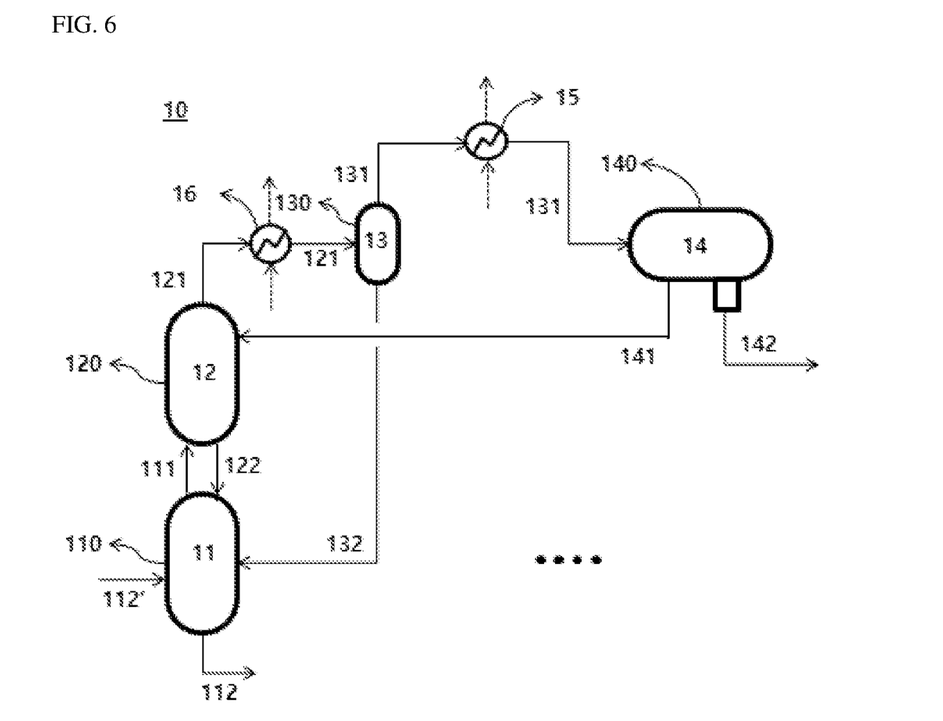
FIG. 6 is a process diagram showing an example of selecting positions of a flash drum lower line and an organic layer line of a diester-based material production unit according to an embodiment of the present invention.
Figure 7:
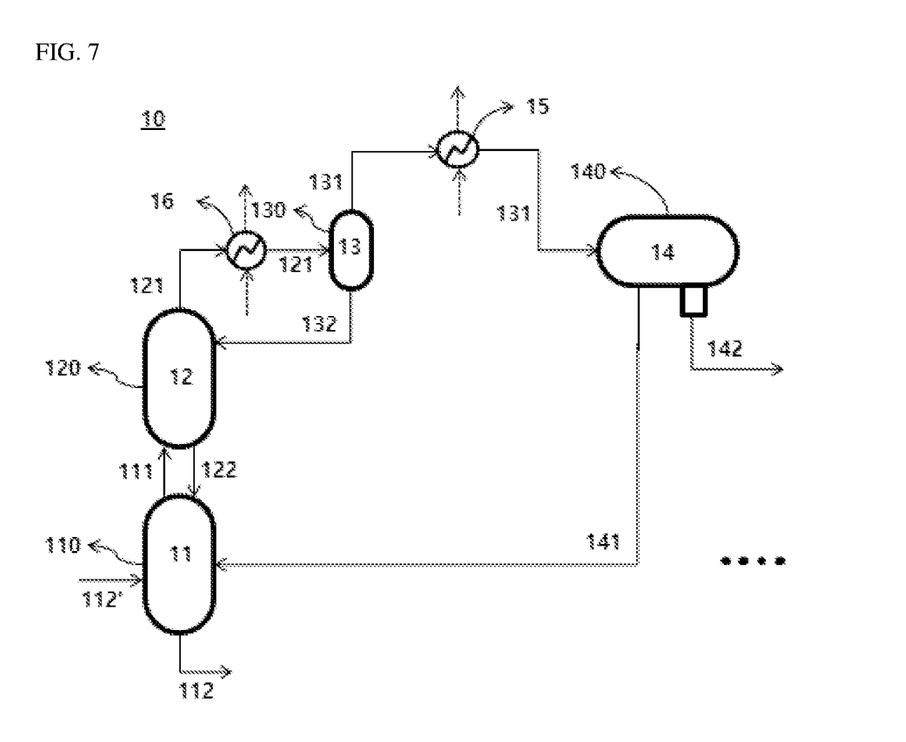
FIG. 7 is a process diagram showing an example of selecting positions of a flash drum lower line and an organic layer line of a diester-based material production unit according to an embodiment of the present invention.

In addition, FIG. 5 illustrates that the connection to the side upper portion of the column main body 120 of the column 12 is achieved through the organic layer line 141 of the layer separator 14 and the flash drum lower line 132 is connected to the side lower portion of the column main body 120. FIG. 6 and FIG. 7 illustrate examples in which the flash drum lower line 132 and the organic layer line 141 are connected to the side upper portion of the column main body 120 and the reaction vessel 110, respectively.

As described above, in FIGS. 2 to 7, it can be confirmed that either one of the flash drum lower line 132 and the organic layer line 141 is necessarily connected to the side upper portion of the column main body 120 of the column 12. As described above, it is only necessary to have a line connected to the side upper portion of the column main body 120 of the column 12. However, it can be appropriately configured in consideration of the fact that the organic layer line 141 of the layer separator 14 has a low stream temperature, so that the effect cannot be great in terms of the volume of steam supplied from the reaction device 11 to the reaction vessel, and when introduced into the side lower portion of the column main body 120, it can be difficult to expect an improvement in gas-liquid separation efficiency in the column 12.

A shown in FIGS. 2 to 4, it is preferable that the flash drum lower line 132 and the organic layer line 141 are connected.

According to an embodiment of the present invention, provided are a reaction part in which two or more of the above-described diester-based material production unit are connected in series, and a purification unit for purifying a reaction product discharged from the reaction part.

The above-described production unit of a diester-based material can be one reactor constituting a portion of the 'reaction part' in view of the entire process. In the present invention, in a continuous process of producing a diester-based material, it is preferable that two or more of the production unit are connected, preferably 3 to 6 or 3 to 5.

When two or more of the production unit 10 are connected, a product produced in the reaction device 11 can be discharged through the product line 112 and moved to the next production unit. " . . . " represented in FIGS. 1 to 8 can be interpreted as an expression that two or more production units can be coupled.

Specifically, the continuous process of producing a diester-based material can include a first production system including a first reaction part in which a direct esterification reaction is performed and a first purification unit in which a product of the first reaction part is purified, and a second production system including a second reaction part in which a trans-esterification reaction with a diester generated is performed through an additional injection of alcohol, and a second purification unit in which a product of the second reaction part is purified. Furthermore, a wastewater treatment unit or a mixed alcohol separation unit can be included.

The production unit according to an embodiment of the present invention can particularly relate to the first reaction part in the first production system in which a direct esterification reaction is performed. However, even if the first purification unit, the second reaction unit, and the second purification unit at a rear end are not connected together, a reaction process is not particularly limited as long as it is a process in which an alcohol is included as a reactant and water is generated as a by-product in order to reduce the volume of steam and the amount of reflux in the reactor.

EXAMPLES

Hereinafter, the present invention will be described in detail with reference to Examples. However, the following examples are merely illustrative of the present invention and are not intended to limit the scope of the present invention.

In the following Examples and Comparative Examples, a process system according to the method of continuous production of a diester-based material, the method according to the present invention, has been simulated by using CONTINUOUS MODELER in a commercial process simulation program ASPEN PLUS.

Experimental Example 1

In performing simulation using the above program, the simulation has been performed by the process illustrated in FIG. 2, wherein four same production units are coupled, dicarboxylic acid was terephthalic acid and a primary alcohol was 2-ethylhexanol as raw materials, and the molar ratio of the two raw materials was set to 1:3. The temperature of an organic layer including the primary alcohol discharged through the organic layer line 141 was set to 40° C., and the connection position of the flash drum lower line 132 and the organic layer line 141 was varied as shown in Table 1 below. The amount of coolant consumed in the condenser 15 and the total flow rate of a steam flowing in the gas phase line 121 of the column 12 were identified, and values in Table 1 below are relative % assuming that Comparative Example 1-1 is 100%.

TABLE 1

| | Flash drum lower line Connection position | Organic layer line Connection position | Coolant usage amount | Column gas phase line flow rate | | | Amount of heat recovered from heat exchanger |
|---|---|---|---|---|---|---|---|
| | | | | 1st | 2nd | 3rd | |
| Comparative Example 1-1 | — | Column main body side upper portion | 100 | 100 | 100 | 100 | 100 |
| Example 1-1 | Column main body side upper portion | Drum main body side portion | 61 | 155 | 138 | 170 | 263 |
| Example 1-2 | Column main body side upper portion | Column main body side upper portion | 63 | 142 | 124 | 158 | 250 |
| Example 1-3 | Column main body side upper portion | Column main body side lower portion | 63 | 145 | 127 | 161 | 252 |
| Example 1-4 | Column main body side lower portion | Column main body side upper portion | 65 | 148 | 131 | 188 | 330 |
| Example 1-5 | Reaction vessel | Column main body side upper portion | 64 | 200 | 184 | 222 | 353 |
| Example 1-6 | Column main body side upper portion | Reaction vessel | 63 | 169 | 153 | 189 | 288 |

Referring to Table 1 above, it can be confirmed that the gas phase line of the column, that is the flow rate of an upper portion was increased due to the installation of a flash drum, which means that the capacity of the column can be divided with the flash drum. It can be seen that the cooling efficiency was greatly increased by recirculating the liquid phase once in the flash drum before flowing to the condenser.

In addition, in the cases of Examples 1-1 to 1-6, although the amount of reflux was relatively large when compared to Comparative Examples, it can be confirmed that the coolant usage amount was greatly reduced despite the large amount of reflux. Accordingly, it can be confirmed that the amount of heat which can be recovered from the heat exchanger was also increased by 2 to 3 times.

From the above, it can be confirmed that the production unit according to the present invention is an innovative process which can reduce energy loss of the entire process by increasing the amount of heat which can be recovered as well as increasing cooling efficiency by installing a flash drum.

Experimental Example 2

In performing simulation using the above program, the simulation has been performed by the process illustrated in FIG. 2, wherein four same production units are coupled, dicarboxylic acid was terephthalic acid and a primary alcohol was 2-ethylhexanol as raw materials, and the molar ratio of the two raw materials was set to 1:2.5. The temperature of an organic layer including the primary alcohol discharged through the organic layer line 141 was set to 95° C., and the connection position of the flash drum lower line 132 and the organic layer line 141 was varied as shown in Table 2 below. The amount of coolant consumed in the condenser 15 and the total flow rate of a steam flowing in the gas phase line 121 of the column 12 were identified, and values in Table 2 below are relative % assuming that Comparative Example 2-1 is 100%.

TABLE 2

| | Flash drum lower line Connection position | Organic layer line Connection position | Coolant usage amount | Column gas phase line flow rate | | | Amount of heat recovered from heat exchanger |
|---|---|---|---|---|---|---|---|
| | | | | 1st | 2nd | 3rd | |
| Comparative Example 2-1 | — | Column main body side upper portion | 100 | 100 | 100 | 100 | 100 |

TABLE 2-continued

|  | Flash drum lower line Connection position | Organic layer line Connection position | Coolant usage amount | Column gas phase line flow rate | | | Amount of heat recovered from heat exchanger |
|---|---|---|---|---|---|---|---|
|  |  |  |  | 1st | 2nd | 3rd |  |
| Example 2-1 | Column main body side upper portion | Drum main body side portion | 60 | 127 | 130 | 143 | 224 |
| Example 2-2 | Column main body side upper portion | Column main body side upper portion | 64 | 125 | 106 | 137 | 217 |
| Example 2-3 | Column main body side upper portion | Column main body side lower portion | 64 | 127 | 109 | 141 | 219 |
| Example 2-4 | Column main body side lower portion | Column main body side upper portion | 60 | 131 | 114 | 165 | 269 |
| Example 2-5 | Reaction vessel | Column main body side upper portion | 59 | 182 | 166 | 190 | 303 |
| Example 2-6 | Column main body side upper portion | Reaction vessel | 65 | 147 | 131 | 171 | 260 |

Referring to Table 2 above, it can be confirmed that the gas phase line of the column, that is the flow rate of an upper portion was increased due to the installation of a flash drum, which means that the capacity of the column can be divided with the flash drum. It can be seen that the cooling efficiency was greatly increased by recirculating the liquid phase once in the flash drum before flowing to the condenser.

In addition, in the cases of Examples 2-1 to 2-6, although the amount of reflux was relatively large when compared to Comparative Examples, it can be confirmed that the coolant usage amount was greatly reduced despite the large amount of reflux. Accordingly, it can be confirmed that the amount of heat which can be recovered from the heat exchanger was also increased by 2 to 3 times.

From the above, it can be confirmed that the production unit according to the present invention is an innovative process which can reduce energy loss of the entire process by increasing the amount of heat which can be recovered as well as increasing cooling efficiency by installing a flash drum.

[Description of the Reference Numerals or Symbols]

| 10: Production unit | 11: Reaction device |
| 110: Reaction vessel | 111: Gas phase discharge line |
| 112: Product line | 112': Raw material injection line |
| 12: Column | 120: Column main body |
| 121: Gas phase line | 122: Liquid phase line |
| 13: Flash drum | 130: Flash drum main body |
| 131: Flash drum upper line | 132: Flash drum lower line |
| 14: Layer separator | 140: Separation tank |
| 141: Organic layer line | 142: Aqueous layer line |
| 15: Condenser | 16: Heat exchanger |

The invention claimed is:

1. A diester-based material production unit comprising:
a reaction device including a reaction vessel in which an esterification reaction of dicarboxylic acid and a primary alcohol is performed and a gas phase discharge line installed at an upper end of the reaction vessel such that vaporized primary alcohol and water are discharged to a column therethrough;
the column including a column main body in which the gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a side portion of a flash drum such that a mixture stream of a gas-phase primary alcohol and water flows out;
a heat exchanger installed on the gas phase line of the column and removing heat of the gas phase line;
the flash drum including a flash drum main body in which separation of a liquid phase and a gas phase is performed in a mixture stream including the primary alcohol and the water, a flash drum lower line from which the liquid phase including a liquefied primary alcohol is discharged, and a flash drum upper line installed to discharge the mixture stream of the gas-phase primary alcohol and the water to a layer separator;
a condenser installed on the flash drum upper line to liquefy the mixture stream of the gas-phase primary alcohol and the water in the flash drum upper line; and
the layer separator including a separation tank in which a layer separation of a mixture of the liquefied primary alcohol and the water into an organic layer and an aqueous layer is performed, an organic layer line through which the separated organic layer is discharged, and an aqueous layer line through which the separated aqueous layer is discharged, wherein:
the flash drum lower line is connected to one or more positions selected from the group consisting of a column main body side upper portion, a column main body side lower portion, and the reaction vessel;
the organic layer line is connected to one or more positions selected from the group consisting of a flash drum main body side portion, the column main body side upper portion, the column main body side lower portion and the reaction vessel; and
at least one of the flash drum lower line and the organic layer line is connected to the column main body side upper portion.

2. The diester-based material production unit of claim 1, wherein the flash drum lower line is connected to the column main body side upper portion.

3. The diester-based material production unit of claim 1, wherein the organic layer line is connected to the flash drum main body side portion or to the column main body side upper portion.

4. The diester-based material production unit of claim 1, wherein the flash drum lower line is connected to the column main body side upper portion, and the organic layer line is connected to the flash drum main body side portion.

5. The diester-based material production unit of claim 1, wherein the dicarboxylic acid comprises one or more selected from the group consisting of terephthalic acid, phthalic acid, isophthalic acid, and cyclohexane dicarboxylic acid.

6. The diester-based material production unit of claim 1, wherein the primary alcohol has 3 to 10 carbon atoms.

7. The diester-based material production unit of claim 1, wherein the esterification reaction is performed at a temperature of 150° C. to 230° C.

8. The diester-based material production unit of claim 1, wherein the temperature of a stream in the gas phase line of the column is 130° C. to 180° C.

9. A diester-based material production system comprising:
    a reaction part in which two or more of the diester-based material production units of claim 1 are connected in series; and
    a purification unit which purifies a reaction product discharged from the reaction part.

10. The diester-based material production system of claim 9, wherein in the reaction part, 3 to 6 production units are connected in series.

* * * * *